(12) United States Patent
Pinnau et al.

(10) Patent No.: US 6,316,684 B1
(45) Date of Patent: Nov. 13, 2001

(54) FILLED SUPERGLASSY MEMBRANE

(75) Inventors: Ingo Pinnau, Palo Alto; Zhenjie He, Fremont, both of CA (US)

(73) Assignee: Membrane Technology and Research, Inc., Menlo Park, CA (US)

(*) Notice: Subject to any disclaimer, the term of this patent is extended or adjusted under 35 U.S.C. 154(b) by 0 days.

(21) Appl. No.: 09/387,802

(22) Filed: Sep. 1, 1999

(51) Int. Cl.$^7$ .......................... C07C 7/144; B01D 65/00; B01D 39/14; B01D 39/00

(52) U.S. Cl. .................... 585/818; 585/819; 210/500.21; 210/500.26; 210/500.27; 210/500.28

(58) Field of Search .................................... 585/816, 819, 585/818; 210/500.21, 500.26, 500.27, 500.28

(56) References Cited

U.S. PATENT DOCUMENTS

| | | |
|---|---|---|
| 4,093,515 | 6/1978 | Kolobow ................................ 195/1.8 |
| 4,279,752 | 7/1981 | Sueoka et al. ...................... 210/500.2 |
| 4,925,562 | 5/1990 | Hennepe et al. ................. 210/500.25 |
| 5,173,189 | 12/1992 | Hoshi et al. ........................... 210/640 |
| 5,281,255 | 1/1994 | Toy et al. ................................. 95/50 |
| 5,707,423 | 1/1998 | Pinnau et al. ............................ 95/45 |
| 5,755,967 | 5/1998 | Meagher et al. ...................... 210/640 |

OTHER PUBLICATIONS

R. M. Barrer, "Diffusion and Permeation in Heterogeneous Media," in *Diffusion in Polymers*, Crank and Park, (eds.) Academic Press, London, 1968.

J. H. Petropoulos, "Mechanisms and Theories for Sorption and Diffusion of Gases in Polymers," in Polymeric Gas Separation Membranes, Paul and Yampolskii, (eds.) CRC Press, Florida, 1994.

S. Ulutan et al., "Separability of ethanol and water mixtures through PTMSP–silica membranes in pervaporation," J. Memb. Sci, 143, 275–284 (1998).

J. P. Boom et al., "Transport through zeolite filled polymeric membranes," J. Memb. Sci, 138, 237–258 (1998).

S. Kumar et al., "Permeation in filled membranes: Role of solute–filler interactions," J. Memb. Sci, 134, 225–233 (1997).

A. Jonquieres et al., "Filled and unfilled composite GFT PDMS membranes for the recovery of butanols from dilute aqueous solutions," J. Memb. Sci, 125, 245–255 (1997).

M. Moaddeb et al., "Effects of colloidal silica incorporation on oxygen/nitrogen separation properties in ceramic–supported 6FDA–IPDA thin films," J. Memb. Sci, 111, 283–290 (1996).

M. Moaddeb et al., "Gas transport properties of thin polymeric membranes in the presence of silicon dioxide particles," J. Memb. Sci, 125, 143–163 (1997).

*Primary Examiner*—Walter D. Griffin
*Assistant Examiner*—Tam M. Nguyen
(74) *Attorney, Agent, or Firm*—J. Farrant (57) ABSTRACT

A membrane and membrane separation process useful in gas, vapor and liquid separations. The membrane comprises a separating layer of a polymer that is characterized by a high glass transition temperature, $T_g$, such as at least about 100° C., and a high free volume within the polymer material itself, such as a fractional free volume of at least about 0.20. Within the polymer material are dispersed fine non-porous particles, such as silica or carbon black particles, having an average diameter no greater than about 1,000 Å. The membrane is particularly useful for separating $C_{3+}$ hydrocarbons from other gases.

38 Claims, 4 Drawing Sheets

FILLED SUPERGLASSY MEMBRANE

This invention was made with Government support under Contract Number DMI-9760767, awarded by the National Science Foundation. The Government has certain rights in this invention.

FIELD OF THE INVENTION

The invention relates to separation membranes. In particular, the invention relates to membranes for gas separation and gas separation processes.

BACKGROUND OF THE INVENTION

Separation membranes are in use in many fields, such as gas separation, pervaporation, ultrafiltration, reverse osmosis, dialysis and electrodialysis.

The optimum separation membrane combines high selectivity with high flux. Thus the membrane industry has engaged in an ongoing quest for membranes with improved flux/selectivity performance. Gas separation is a particularly active research area.

In recent years, some glassy polymer materials with extremely high gas permeabilities have been synthesized and formed into membranes. The best known and most studied of these is poly(1-trimethylsilyl-1-propyne) [PTMSP], a substituted polyacetylene.

PTMSP has been found to exhibit anomalous properties for a glassy material, in that PTMSP membranes are more permeable to larger, more condensable molecules than to smaller, less condensable molecules. Also, they have higher mixed gas selectivity than pure gas selectivity for at least some gas pairs. These properties were made use of in U.S. Pat. No. 5,281,255, for example. PTMSP has become known as a "superglassy" material, in part because of the unusual combination of permeability and selectivity properties.

Other polyacetylenes are known that exhibit superglassy properties similar to those of PTMSP. For example, U.S. Pat. No. 5,707,423 describes hydrocarbon-based polymers that exhibit selectivity in favor of condensable organic molecules over smaller, less condensable molecules, and in which measured mixed gas selectivity is higher than calculated pure gas selectivity.

It is known to incorporate various types of small particles, generally called fillers, into polymeric membranes to modify the membrane properties. U.S. Pat. No. 4,093,515 discloses a membrane using multiple layers of silicone rubber polymer, in which one layer contains a silica filler and another contains a carbon black filler. The membrane is used in an artificial lung for blood oxygenation during surgery.

U.S. Pat. No. 4,279,752 discloses a poly(vinyl alcohol) membrane prepared from a solution containing colloidal silica particles or silica powder. In this case, most of the silica is subsequently leached out to form a microporous membrane.

U.S. Pat. No. 4,925,562 discloses silicone rubber membranes filled with zeolite particles. The membrane is used to separate alcohols from water, for example.

U.S. Pat. No. 5,173,189 describes the incorporation of unspecified particles into a support for a membrane used for organic solvent/water separations.

U.S. Pat. No. 5,755,967 also concerns a silicone rubber membrane filled with zeolite. In this case the membrane is used to separate butanol and other products from fermentation broth.

A chapter by J. H. Petropoulos entitled "Mechanism and Theories for Sorption and Diffusion of Gases in Polymers" in *Polymeric Gas Separation Membranes*, D. R. Paul and Yu. P. Yampol'skii (eds.), CRC Press, 1994, presents equations and graphs indicating the effect on permeability of the presence of a less-permeable phase dispersed in a more-permeable phase.

A chapter by R. M. Barrer entitled "Diffusion and Permeation in Heterogeneous Media" in *Diffusion in Polymers*, J. Crank and G. S. Park (eds.), Academic Press, 1968, presents several theoretical treatments and experimental data showing the decrease in permeability that occurs when impermeable particles are dispersed in a permeable polymer.

A paper by A. Jonquieres and A. Fane entitled "Filled and unfilled composite GFT PDMS membranes for the recovery of butanols from dilute aqueous solutions: influence of alcohol parity", in *Journal of Membrane Science*, Vol. 125, pages 245–255 (1997) discusses the use of filled silicone rubber membranes for butanol/water separations. The filled membranes provide lower fluxes but higher selectivity than their unfilled membranes.

A paper by S. Kumar et al. entitled "Permeation in filled membranes: Role of solute-filler interactions" in *Journal of Membrane Science*, Vol. 134, pages 225–233 (1997) compares theoretical and experimental results for pervaporation of alcohols and carboxylic acids through filled membranes containing adsorptive fillers. The paper points out that filled membranes, because of their reduced permeability, can be used for as barrier materials in packaging.

A paper by J. P. Boom et al. entitled "Transport through zeolite filled polymeric membranes", in *Journal of Membrane Science*, Vol. 138, pages 237–258 (1998) includes experimental results and numerical modeling studies of separation of methanol/toluene mixtures by means of rubbery membranes containing hydrophilic and hydrophobic zeolites.

A paper by S. Ulutan and T. Nakagawa entitled "Separability of ethanol and water mixtures through PTMSP-silica membranes in pervaporation", in *Journal of Membrane Science*, Vol. 143, pages 275–284 (1998) discusses ethanol/water separation pervaporation experiments performed with membranes in which large silica particles with average diameters of 5 $\mu$m were loaded asymmetrically into a PTMSP membrane. The loaded membranes had poorer separation factors than the pure PTMSP membranes.

A paper by M. Moaddeb and W. J. Koros entitled "Effect of colloidal silica incorporation on oxygen/nitrogen separation properties of ceramic-supported 6FDA-IPDA thin films" in *Journal of Membrane Science*, Vol. 111, pages 283–290 (1996) discusses a membrane formed on a ceramic support. The support material is coated with silica particles, which impregnate the pores of the support surface. The structure is then coated with a polyimide solution. The resulting membrane exhibits improved properties for oxygen/nitrogen separation.

Another paper by Moaddeb and Koros entitled "Gas transport properties of thin polymeric membranes in the presence of silicon dioxide particles" in *Journal of Membrane Science*, Vol. 125, pages 143–163 (1997) provides additional experimental data and discussion compared with the earlier paper. The polymers used are conventional glassy materials with low free volumes ranging from 0.16 to 0.19. The paper reports an increase in oxygen/nitrogen selectivity and an apparent increase in oxygen permeability compared with films of polymer alone.

SUMMARY OF THE INVENTION

The invention is a membrane useful in gas, vapor and liquid separations in one aspect, and in another aspect is separation processes using the membrane. The membrane comprises a separating layer of a polymer that is characterized by a high glass transition temperature, $T_g$, such as at least about 100° C., and a high free volume within the polymer material itself, such as a fractional free volume of at least about 0.20. Within the polymer material are dispersed fine non-porous particles, such as silica or carbon black particles.

Representative examples of high-free-volume polymers of which the membrane can be formed include certain substituted polyacetylenes, certain polydioxole copolymers and certain polyimides. A particularly preferred polymer material is poly(4-methyl-2-pentyne) [PMP]. All of these materials have been used to form the discriminating layer of a separation membrane before; however they have not been used in the filled form of the present invention. The preferred filler material is very fine silica, by which we mean silica with an average particle diameter of less than about 1,000 Å, and the loading of filler is preferably high, such as more than about 20 wt %.

The filled membranes exhibit unexpected properties. In prior art studies, the gas permeability of polymer materials has been found to be decreased by adding a non-porous filler. This is consistent with the theoretical treatments of Barrer, Petropoulos and others, and the fact that the average path length traversed by a permeating gas molecule is increased, as the molecules cannot pass through the particles, but must diffuse around them. In contrast, we found that the filled polymer materials of the invention exhibit higher gas permeabilities than their unfilled counterparts. This increase in permeability in some cases is very large, such as 40%, 80%, or more than 100%.

For most polymer materials, there is also a trade-off between permeability and selectivity. In general, materials with high permeability have comparatively low selectivity for one gas over another, and highly selective materials are comparatively impermeable to all gases. Thus, one would normally expect an increase in permeability to be accompanied by a decrease in discriminating capability or selectivity. Again, in contrast, we found that the filled polymer materials of the invention exhibit higher selectivity for some gas pairs, such as a larger hydrocarbon and a smaller hydrocarbon, or a hydrocarbon and a permanent gas, than their unfilled counterparts. This increase in selectivity was again large in some cases, such as 20%, 50%, or more than 100%.

These combined permeability/selectivity properties are, therefore, unusual, and provide performance advantages in a variety of separations.

The membranes of the invention may be made by solution casting or coating, or any other convenient method, and may be made as unsupported films, integral asymmetric membranes, composite membranes, or any other suitable structure. The membranes may be prepared in any form, such as flat sheet, hollow fiber, tubular or other, and may be housed in any appropriate type of module, such as plate-and-frame, potted fiber, or spiral-wound.

In another aspect, the invention is a separation process using the membrane. In its most basic aspect, the process comprises the following steps:

(a) providing a membrane having a feed side and a permeate side, the membrane comprising a separating layer of a polymer having a glass transition temperature, $T_g$, of at least about 100° C. and a fractional free volume of at least about 0.20, within which polymer material are dispersed fine non-porous particles having an average particle diameter no greater than about 1,000 Å;

(b) passing a first fluid mixture containing a component to be separated across the feed side;

(c) providing a driving force for transmembrane permeation;

(d) withdrawing from the permeate side a second fluid mixture enriched in the component compared with the first fluid mixture.

The fluid mixture to be separated can be gases or liquids. The membranes are believed to be particularly useful for the separation in the gas phase of a condensable organic component from a less condensable organic or inorganic compound, or of $C_{3+}$ hydrocarbon components from multi-component gas streams, such as natural gas and refinery gas streams. The membranes are also believed to be useful for liquid-phase separations, such as pervaporation, including the separation of dissolved organics from water, and the separation of organic liquid mixtures.

For some hydrocarbon separation processes, such as separation of unsaturated from saturated hydrocarbons, we believe that filled polymers of lower free volume than 0.20 may also be useful within the scope of the invention.

It is an object of the invention to provide highly permeable membrane materials.

It is an object of the invention to provide a membrane combining high permeability and useful selectivity for a number of gases.

It is an object of the invention to provide membranes and processes useful for separating or enriching a gas from a fluid mixture.

It is an object of the invention to provide membranes and processes for separating a component from a fluid mixture.

It is an object of the invention to provide membranes and processes for natural gas liquids (NGL) recovery.

It is an object of the invention to provide membranes and processes for refinery process stream treatment.

Additional objects and advantages will be apparent from the description of the invention to those skilled in the art.

It is to be understood that the above summary and the following detailed description are intended to explain and illustrate the invention without restricting its scope.

DETAILED DESCRIPTION OF THE INVENTION

The term gas as used herein means a gas or a vapor.

The term fluid as used herein means a gas, vapor or liquid.

The term $C_{3+}$ hydrocarbon means a straight- or branched-chain hydrocarbon having at least three carbon atoms.

The term unsaturated hydrocarbon means a hydrocarbon having at least one carbon-carbon double bond or at least one carbon-carbon triple bond.

The terms ideal selectivity and pure gas selectivity as used herein mean the selectivity for one material over another as calculated from permeation measurements with the components singly.

The term substituted acetylene as used herein means a molecule of acetylene, that is $C_2H_2$, in which at least one of the hydrogen atoms has been replaced by another atom or group of atoms.

The term substituted polyacetylene as used herein means a polymer having repeating units of a substituted acetylene.

All permeabilities cited herein are at room temperature unless otherwise stated.

In its first aspect, the invention is a membrane useful for gas, vapor, and liquid separations. The membrane comprises a separating layer that itself comprises a polymer characterized by a high glass transition temperature, a high free volume within the polymer material itself and an unusually high permeability.

The glass transition temperature, $T_g$, is at least above 100° C., and may be much higher, such as above 150° C. or above 200° C. This means the separating layer is completely rigid and glassy under the conditions in which it is used in the process of the invention.

The free volume is an intrinsic property of the polymer material itself and can be expressed as fractional free volume (free volume/cm$^3$ of polymer) or specific free volume (free volume/g of polymer). The free volume is calculated from the expressions:

Specific free volume=$v_{sp}-v_0=v_{sp}-1.3v_w$

Fractional free volume=(specific free volume)/$v_{sp}$ where $v_{sp}$ is the specific volume (cm$^3$/g) of the polymer as determined from density or thermal expansion measurements, $v_0$ is the zero point volume at 0° K., and $v_w$ is the van der Waals volume, calculated by the group contribution method of Bondi. The fractional free volume of the polymers particularly suitable for use in the invention is at least 0.20 and may be higher, such as 0.22, 0.25 or 0.30 or higher. For example, poly(1-trimethylsilyl-1-propyne) [PTMSP], a silicon-substituted polyacetylene, has a typical fractional free volume of about 0.28 according to this method, poly(4-methyl-2-pentyne) [PMP] has a fractional free volume of about 0.27 and Teflon® AF, a block copolymer of a fluorodioxole unit and a tetrafluoroethylene unit, has a fractional free volume of about 0.33, depending on grade. In contrast, conventional glassy polymers typically have fractional free volumes of less than 0.20, such as 0.164 for polycarbonate, or 0.190 for 6FDA-6FpDA polyimide. Rubbery polymers also have lower fractional free volumes, such as 0.18 for silicone rubber.

The high permeability of the polymers is characterized by the nitrogen permeability, which should be, at room temperature, at least about 50 Barrer, and may be higher, such as 100 Barrer. Typically, the polymers also exhibit hydrocarbon permeability of at least about 300 Barrer for methane, at least about 500 Barrer for propane and at least about 1,000 Barrer for n-butane.

Non-limiting examples of polymer materials that fall within the definition of glassy, high-free-volume, high-permeability materials useful for forming the membranes and carrying out the processes of the invention include:

(i) Substituted acetylenes, having the general structural formula (1)

where $R_1$ and $R_2$ are independently hydrogen, a halogen, phenyl or a linear or branched $C_1$–$C_4$ alkyl group, and n is a positive integer.

(ii) disubstituted polyacetylenes, having the general formula:

(2)

wherein $R_1$ is chosen from the group consisting of $C_1$–$C_4$ alkyl and phenyl, and wherein $R_2$ is chosen independently from the group consisting of hydrogen and phenyl.

(iii) Silicon-containing polyacetylenes, having the general structural formula (3)

where $R_1$ is a linear or branched $C_1$–$C_4$ alkyl group, $R_2$ and $R_3$ are independently linear or branched $C_1$–$C_6$ alkyl groups, and $R_4$ is a linear or branched $C_1$–$C_{12}$ alkyl or aryl group, and m is a positive integer.

(iv) Silicon-containing polyacetylenes, having the general structural formula (4)

where $R_1$ is phenyl or a linear or branched $C_1$–$C_4$ alkyl group, $R_2$ and $R_3$ are independently linear or branched $C_1$–$C_6$ alkyl groups, $R_4$ is a linear or branched $C_1$–$C_{12}$ alkyl or aryl group, and X is phenyl or a $C_1$–$C_3$ alkyl group, and m and n are independently positive integers.

(v) Germanium-containing polyacetylenes, having the general structural formula (5)

where $R_1$ is a linear or branched $C_1-C_4$ alkyl group, $R_2$ and $R_3$ are independently linear or branched $C_1-C_6$ alkyl groups, $R_4$ is a linear or branched $C_1-C_{12}$ alkyl or aryl group, and X is a $C_1-C_3$ alkyl group, and m and n are independently positive integers.

(vi) Polymers and copolymers of perfluoro-2,2-dimethyl-1,3-dioxole.

Specific polymers that can be used include poly(1-trimethylsilyl-1-propyne) [PTMSP], poly(4-methyl-2-pentyne) [PMP], and poly(2,2-bistrifluoromethyl-4,5-difluoro-1,3-dioxole) [Teflon® AF]. The most preferred polymer material is PMP, which has repeating units of the structure:

(6)

PMP is highly chemically resistant, being insoluble in many common organic solvents, such as aromatic hydrocarbons and chlorinated hydrocarbons. The only solvents we have found to be capable of fully dissolving PMP are cyclohexane, methylcyclohexane and carbon tetrachloride. This is an advantageous property, in that it enables membranes manufactured from this material to withstand harsh environments of use, and renders them workable in situations where more soluble polymers might lose performance or be subject to catastrophic failure.

The separating layer may also comprise blends or copolymers of the above-defined polymers with other polymers.

The separating layer further comprises particles dispersed within the polymer. The filler particles are characterized by being non-porous and fine. By fine, we mean having an average particle diameter preferably no more than about 1,000 Å, more preferably not more than about 500 Å, and most preferably no more than about 200 Å. The fineness of the particles can also be expressed as specific surface area ($m^2/g$); in these terms the particles should preferably have an average specific surface area of at least about 100 $m^2/g$, more preferably at least about 150 $m^2/g$ and most preferably at least about 200 $m^2/g$. Non-limiting examples of non-porous filler materials useful for forming the membranes and carrying out the processes of the invention include silica, carbon black, ferrous oxide, aluminum oxide, titanium oxide, calcium carbonate, barium sulfate and the like. The particles may be surface treated to modify their properties, such as by adding hydrophilic or hydrophobic surface groups.

As a general guideline, the higher the proportion of filler particles incorporated into the membrane layer, the more are the separation properties enhanced. Thus, it is preferred that the particle loading (expressed as weight of particles/weight of (polymer plus particles)×100% ) be high, such as at least about 20 wt %, more preferably at least about 30 wt %, and most preferably at least about 40 wt %.

The membranes may be made by any technique known in the art. Because the polymers are glassy and rigid, an unsupported film, tube or fiber of the filled polymer may be usable as a single-layer membrane. In this case, the preferred method of manufacture is to prepare a solution of the membrane polymer, to mix the filler particles into the solution, and to cast the resulting dispersion onto a glass plate or a removable or non-removable backing web, according to general casting procedures that are well known in the art. The resulting flat-sheet membrane films may be dried under ambient conditions, at elevated temperature, or under vacuum as desired to produce thin film membranes. Alternatively, the membrane may be manufactured in the form of hollow fibers, the general methods for preparation to which are copiously described in the literature, for example in U.S. Pat. No. 3,798,185 to Skiens et al., incorporated herein by reference.

As a further alternative, the separation membrane of the invention may be incorporated into a composite membrane, that is, a membrane having multiple layers, including a highly permeable but relatively unselective support layer, which provides mechanical strength, and the comparatively thin selective membrane layer of filled polymer that contributes to or is primarily responsible for the separation properties. Composite membranes in accordance with the invention may be made by preparing a polymer solution containing dispersed filler particles, as described above, coating the support membrane with this solution, and allowing the solvent to evaporate. General preparation techniques for making composite membranes of this type are well known, and are described, for example, in U.S. Pat. No. 4,243,701 to Riley et al., incorporated herein by reference. Again, the membrane may take flat-sheet, tube or hollow-fiber form. The most preferred support membranes are those with an asymmetric structure, which provides a smooth, comparatively dense surface on which to coat the selective layer. Support membranes are themselves frequently cast onto a backing web of paper or fabric. As an alternative to coating onto a support membrane, it is also possible to make a composite membrane by solution-casting the polymer directly onto a non-removable backing web.

Whether the membrane is prepared in the form of a single layer, an asymmetric membrane or a composite membrane, it is preferred that the filler particles be well dispersed through the polymer layer so that the polymer/filler composition is at least roughly uniform throughout. It is preferred, therefore, that the dispersion containing the particles be very well mixed immediately before it is cast or coated as described above.

The thickness of the filled polymer separation membrane or membrane layer can be chosen according to the proposed use, and may vary from a few microns or less up to hundreds of microns.

Once formed, the membranes of the invention may be used in any appropriate type of separation device. We prefer to prepare the membranes in composite, flat-sheet form and to house them in spiral-wound modules. However, flat-sheet membranes may also be mounted in plate-and-frame modules or in any other way. If the membranes are prepared in the form of hollow fibers or tubes, they may be potted in cylindrical housings or otherwise. For use, the membrane modules may be assembled in one-stage or multi-stage arrangements as needed to meet processing capacity.

It is anticipated that the membranes of the invention will be useful in a number of separation applications. Thus, in another aspect, the invention is a process for separating a component from a fluid mixture. In its most basic embodiment, the invention in this aspect comprises:

(a) providing a membrane having a feed side and a permeate side, the membrane comprising a separating layer of a polymer having a glass transition temperature, $T_g$, of at least about 100° C. and a fractional free volume of at least about 0.20, within which polymer material are dispersed fine non-porous particles having an average particle diameter no greater than about 1,000 Å;

(b) passing a first fluid mixture containing a component to be separated across the feed side;

(c) providing a driving force for transmembrane permeation;

(d) withdrawing from the permeate side a second fluid mixture enriched in the component compared with the first fluid mixture.

The driving force for permeation across the membrane is generally provided by providing a pressure difference between the feed and permeate sides. This can be generated in a variety of ways, such as by compressing the feed stream, by drawing a vacuum on the permeate side of the membrane, by condensing the permeate stream, or by combinations of these. Sometimes the stream to be treated may already be at a high enough superatmospheric pressure to provide adequate transmembrane driving force without additional compression on the feed side or lowering of pressure on the permeate side.

The fluids on the feed and permeate sides may be gases or liquids. If both fluids are gases, then the process is gas separation, and includes the following steps:

(a) providing a membrane having a feed side and a permeate side, the membrane comprising a separating layer of a polymer having a glass transition temperature, $T_g$, of at least about 100° C. and a fractional free volume of at least about 0.20, within which polymer material are dispersed fine non-porous particles having an average particle diameter no greater than about 1,000 Å;

(b) passing a first gas mixture containing a component to be separated across the feed side;

(c) providing a driving force for transmembrane permeation;

(d) withdrawing from the permeate side a second gas mixture enriched in the component compared with the first gas mixture.

Membranes that comprise the above-defined filled polymers as the selective layer exhibit generally high pure gas permeabilities and low selectivities calculated from pure gas measurements. For example, for many gas pairs the calculated pure gas selectivity is lower than 5. As reported in the Examples section below, we found that the measured mixed-gas selectivity for mixtures of condensable and non-condensable gases, such as hydrocarbons with air, nitrogen or hydrogen, or more condensable and less condensable gases, such as propane with methane or butane with methane, is often better than the calculated ideal, or pure gas, selectivity. For example, for many of these gas pairs, including but not limited to, n-butane/methane, n-butane/hydrogen, propane/nitrogen, propylene/hydrogen and propane/hydrogen, a measured selectivity is at least about 10, and frequently higher, such as 15, 20, 25 or more can be achieved with one or more of the polymer/filler combinations taught herein. Superglassy polymers are believed to contain large, interconnected free-volume elements that give rise to a gas transport mechanism that is intermediate between solution/diffusion and pore flow. The free-volume elements may become blocked by sorption of the more condensable component, thereby reducing transport of the less condensable component and increasing selectivity. As mentioned in the background section above, normally a non-porous filler lowers polymer permeability by increasing the path length traversed by the average gas molecule as it permeates the material. In the case of superglassy polymers, however, we believe that suitably sized fine particles interfere with the polymer packing, inhibiting the ability of the rigid polymer chains to pack into their normal equilibrium state. The result is a yet more open structure, which seems, as we found by experiment, to lead to higher permeability combined with higher selectivity for certain separations. The permeability of the filled membranes of the invention to most gases, including oxygen, carbon dioxide, hydrogen, methane, propane and n-butane is at least about 1,000 Barrer, and often higher, such as 2,000 Barrer, or even 5,000 Barrer or above.

In light of these properties, the membranes of the invention that comprise a selective layer of the defined polymers are especially useful for the following gas separation processes. This list is intended to be exemplary, not limiting:

Separation of condensable components having boiling points at atmospheric pressure of −100° C. or above from other gases with lower boiling points Separation of condensable components having boiling points at atmospheric pressure of −50° C. or above from other gases with lower boiling points Separation of organic components, especially hydrocarbon vapors, from air or other gases Separation of mixtures of organic vapors, especially hydrocarbon vapors, of different boiling points Separation of components of natural gas streams, especially removal of $C_{3+}$ hydrocarbons Separation of refinery process and off-gas streams containing mixed hydrocarbons or hydrocarbon/hydrogen mixtures Separation of components of petrochemical manufacturing streams Separation of low-boiling gases from one another, for example methane from nitrogen, in the presence of a condensable gas.

At present, our most preferred process for which the new membranes are useful is the separation of hydrocarbons from hydrogen in refinery and petrochemical process and off-gas streams. Many operations carried out in refineries and petrochemical plants involve feeding a hydrocarbon/hydrogen stream to a reactor, withdrawing a reactor effluent stream of different hydrocarbon/hydrogen composition, separating the effluent into liquid and vapor portions, and recirculating part of the vapor stream to the reactor, so as to reuse unreacted hydrogen.

Reactions carried out under such a scheme can be divided generally into hydrogen-consuming reactions and hydrogen-producing reactions. The hydrogen-consuming reactions include hydrotreating, hydrocracking and various hydrogenation operations. The hydrogen-producing reactions include reforming and various dehydrogenation operations. Whether the reaction produces or consumes hydrogen, it is always desirable to recover as much hydrogen as possible for reuse in the process or as a net hydrogen stream for use elsewhere. Before the hydrogen can be further used or reused, it is usually necessary to purify it by removing other gas components, particularly higher hydrocarbons. Membranes have already been used for this separation step, particularly for high-pressure and high-hydrogen-concentration streams. However, conventional glassy membranes are selectively permeable to hydrogen over hydrocarbons, so that the purified hydrogen is concentrated in the low pressure permeate stream and has to be recompressed before it can be used or reused. The processes of the invention have the advantage that the purified hydrogen stream is retained as the residue on the high-pressure side of the membrane, so that recompression is not required. Representative hydrogen- and hydrocarbon-containing gas mixtures that can be treated by the processes of the invention include process and off-gases from: hydrocrackers; hydrotreaters of various kinds, including hydrodesulfurization units; catalytic crackers; coking reactors; catalytic reformers; specific isomerization, alkylation and dealkylation units; steam reformers; hydrogenation and dehydrogenation processes; and steam crackers for olefin production.

In the case of these hydrogen/hydrocarbon separations, the process of the invention comprises:

(a) providing a membrane having a feed side and a permeate side, the membrane comprising a separating layer of a polymer having a glass transition temperature, $T_g$, of at least about 100° C. and a fractional free volume of at least about 0.20, within which polymer material are dispersed fine non-porous particles having an average particle diameter no greater than about 1,000 Å;

(b) passing a gas mixture comprising $C_{3+}$ hydrocarbons and hydrogen across the feed side;

(c) providing a driving force for transmembrane permeation;

(d) withdrawing from the permeate side a permeate gas mixture enriched in $C_{3+}$ hydrocarbons compared with the gas mixture;

(e) withdrawing from the feed side a residue gas mixture enriched in hydrogen compared with the gas mixture.

In all of these hydrocarbon/hydrogen separation processes, the membranes of the invention offer some specific advantages. In the first place, they can exhibit good mixed-gas selectivity, such as about 10 or more for propylene over hydrogen. In the second place, they exhibit high transmembrane $C_{3+}$ hydrocarbon fluxes, such as $1\times10^{-4}$ cm$^3$(STP)/cm$^2$·s·cmHg, which means that large amounts of gas can be processed per unit area of membrane used. As mentioned above, the $C_{3+}$ hydrocarbons permeate the membrane and the hydrogen-enriched gas remains on the feed side at high pressure. Finally, particularly if PMP is used, they resist dissolution by most of the hydrocarbon components typically found in refinery and petrochemical process streams. This is valuable, since it enables the membranes to withstand feeds saturated with aromatic components, plant upsets that might bring the membranes into contact with hydrocarbon liquids, and other challenging situations.

The membranes can also be used in refinery and petrochemical environments for separating hydrocarbon mixtures into a $C_{3+}$ hydrocarbon enriched permeate and a methane enriched residue. The heavier fraction may then be liquefied as LPG product and the residue stream sent to fuel gas, for example.

Another similar preferred gas separation application of the membranes and processes of the invention is in natural gas processing, such as to separate $C_{3+}$ hydrocarbons from methane. The membranes of the invention are more permeable to the $C_{3+}$ components than to methane, so that the $C_{3+}$ gases and vapors permeate preferentially through the membrane to form a $C_{3+}$ enriched permeate stream. The permeate stream can be at least partially condensed to recover an NGL fraction or subjected to further processing. Depending on the composition of the raw gas, and the process parameters, the process may be tailored to a variety of NGL recovery opportunities. Some specific, non-limiting, examples include: dewpoint control to eliminate condensation of hydrocarbon liquids in the pipeline; Btu control to meet pipeline specification, or to treat gas for use as field engine fuel; NGL recovery from associated gases from oil wells or from gases generated during enhanced oil recovery (EOR); and pretreatment of hydrocarbon-laden gas streams to remove NGL components that may damage other types of membranes, such as cellulose acetate membranes, used during natural gas treatment. In these applications, the process offers an n-butane/methane selectivity as high as 10 or more, combined with high transmembrane $C_{3+}$ hydrocarbon fluxes, such as $1\times10^{-4}$ cm$^3$(STP)/cm$^2$·s·cmHg or above.

In a second exemplary process aspect, the process of the invention can be pervaporation. In this case, the feed fluid is liquid and the permeate fluid is in the gas phase. The process of the invention then includes the following steps:

(a) providing a membrane having a feed side and a permeate side, the membrane comprising a separating layer of a polymer having a glass transition temperature, $T_g$, of at least about 100° C. and a fractional free volume of at least about 0.20, within which polymer material are dispersed fine non-porous particles having an average particle diameter no greater than about 1,000 Å;

(b) passing a liquid mixture containing a component to be separated across the feed side;

(c) providing a driving force for transmembrane permeation;

(d) withdrawing from the permeate side a gas mixture enriched in the component compared with the liquid mixture.

In the case of pervaporation, the driving force for transmembrane permeation may often be conveniently provided, at least in part, by subjecting the permeate stream to condensation, thereby lowering the vapor pressure on the permeate side.

Pervaporation is used industrially to remove water from organic liquids, such as dehydration of alcohols, and is beginning to be used to remove organic compounds from water, such as waste water, process water or groundwater. Much work has also been done at the research level on separation of organic liquids from one another, such as to separate close-boiling liquids or to break azeotropes. The membranes of the invention that comprise a selective layer of the defined polymers are useful for the following representative, but non-limiting, pervaporation processes:

(a) Separation of organic compounds from water. In this regard, the membranes of the invention are particularly useful for:

Removal of hydrocarbons such as benzene, toluene and xylene from process and waste waters.

Separation of alcohols and ketone from product, process or waste streams.

Removal of chlorinated solvents from process and waste waters.

Recovery of flavors and essences in the food processing industry.

Treatment of polluted groundwater to remove volatile organics.

Treatment of organic-containing condensate waters from various sources.

(b) Separation of mixed organic components, particularly those having close boiling points or forming azeotropes. In these processes, the membranes of the invention that exhibit exceptional chemical resistance, such as filled PMP membranes, are particularly valuable.

For some gas and liquid separation processes, membranes incorporating filled layers of comparatively impermeable conventional glassy polymers, such as polyimides, polycarbonate and polysulfone, having fractional free volume lower than 0.20, are useful. These membranes may be prepared as generally described above. In this case, however, it is particularly important to disperse the particles as uniformly as possible within the separating membrane layer to open up the comparatively dense structure of the polymer matrix throughout and thereby improve the permeability of the material. A preferred form of the membrane in this case, therefore, is a composite membrane comprising a highly permeable polymeric support membrane, on which is carried the filled polymer selective layer. The support is preferably in asymmetric form, with a very thin skin side on which the separating or selective layer is preferably deposited by solution coating as described above, using a polymer solution into which the filler particles have been dispersed, and which has been very well mixed prior to the solution coating step. Such composite membranes are believed to be of value in separating mixtures of an unsaturated and a saturated hydrocarbon, for example propylene/propane mixtures, in separating mixtures of branched and linear hydrocarbons, and in separating other mixtures of relatively large, comparatively slowly diffusing molecules on the basis of difference in molecular size.

The invention is now illustrated in further detail by specific examples. These examples are intended to further clarify the invention, and are not intended to limit the scope in any way.

EXAMPLES

SET 1: PMP Experiments and Results

Example 1

Polymer Film Preparation

The polymer, poly(4-methyl-2-pentyne) [PMP], was prepared in accordance with the procedure described in U.S. Pat. No. 5,707,423, incorporated herein by reference in its entirety. The polymer was dissolved in cyclohexane (1–2 wt % solution), and the solution was cast onto glass plates. The resulting films were dried at ambient conditions for 24 hours, then dried under vacuum at 80° C. for three days to completely remove the solvent. The finished PMP films were 20–50 $\mu$m ($\pm 0.5$ $\mu$m) thick, as determined with a precision micrometer.

Example 2

Filled-Polymer Film Preparation

Silica-filled PMP films were prepared by dispersing 10–50 wt % (based on polymer) ultrafine silica particles (Cabot Corp., Tuscola, Ill.) in the PMP casting solution. The dispersion was mixed with a high-speed blender for 10 minutes and cast immediately onto glass plates. The silica-filled PMP films were dried as described in Example 1. The finished filled-PMP films were 50–200 $\mu$m ($\pm 0.5$ $\mu$m) thick, as determined with a precision micrometer. Table 1 lists the characteristics of four different silica types that were used for the filled PMP films.

TABLE 1

| Silica Type | Surface Groups | Surface Area ($m^2/g$) | Approximate average particle diameter (Å) |
|---|---|---|---|
| L-90 | hydroxyl (hydrophilic) | 90 | 350 |
| M-5 | hydroxyl (hydrophilic) | 200 | 150 |
| EH-5 | hydroxyl (hydrophilic) | 380 | 80 |
| TS-530 | trimethylsilyl (hydrophobic) | 210 | 150 |

Example 3

Composite Membrane Preparation

Composite PMP membranes containing 30 wt % of a hydrophilic silica filler (EH-5) were prepared by a continuous solution-coating process. A microporous poly(vinylidene fluoride) [PVDF] support membrane was dip-coated six times with a 2 wt % PMP/EH-5 solution in cyclohexane at a coating speed of 2 ft/min. After each coating step, the membrane was dried at 60° C. for 20 minutes. The PMP/EH-5 composite membrane had a pressure-normalized oxygen flux of $200 \times 10^{-6}$ $cm^3$(STP)/$cm^2 \cdot s \cdot cmHg$ and an oxygen/nitrogen selectivity of 1.8, indicating that the membrane was defect-free.

Examples 4–5

Pure-Gas Permeation Properties of PMP and Filled-PMP Films

Example 4

Effect of Filler Type on Pure-Gas Permeation Properties of Filled-PMP Films

Experiments were carried out to determine the pure-gas permeation properties of the PMP and filled-PMP films prepared in Examples 1 and 2. The filled-PMP films each contained 30 wt % filler. Samples of the films were cut into stamps and mounted in a permeation test-cell apparatus. The permeation of pure nitrogen, oxygen, methane, hydrogen, and carbon dioxide was measured at a feed pressure of 50 psig and a permeate pressure of 0 psig. The temperature was maintained at 25° C. The measurements were carried out with a constant pressure/variable volume method; the volumetric gas flow rates were determined with a bubble flow meter. The pure-gas permeabilities and the calculated selectivities of the filled and unfilled PMP films are shown in Table 2.

TABLE 2

| | Surface Area ($m^2$g) | Permeability (Barrer) | | | | | Selectivity | | | |
|---|---|---|---|---|---|---|---|---|---|---|
| Silica Type | | $N_2$ | $O_2$ | $CH_4$ | $H_2$ | $CO_2$ | $O_2/N_2$ | $CH_4/N_2$ | $H_2/CH_4$ | $CO_2/CH_4$ |
| None (pure PMP) | N/A | 820 | 1,670 | 1,870 | 3,920 | 7,320 | 2.0 | 2.3 | 2.1 | 3.9 |
| Hydrophilic L-90 | 90 | 880 | 2,050 | 2,800 | 4,500 | 9,150 | 2.3 | 3.2 | 1.6 | 3.3 |
| Hydrophilic M-5 | 200 | 1,280 | 2,560 | 3,000 | 5,410 | 11,100 | 2.0 | 2.3 | 1.8 | 3.7 |

TABLE 2-continued

| Silica Type | Surface Area (m²g) | Permeability (Barrer) | | | | | Selectivity | | | |
|---|---|---|---|---|---|---|---|---|---|---|
| | | $N_2$ | $O_2$ | $CH_4$ | $H_2$ | $CO_2$ | $O_2/N_2$ | $CH_4/N_2$ | $H_2/CH_4$ | $CO_2/CH_4$ |
| Hydrophilic EH-5 | 380 | 1,210 | 2,160 | 3,140 | 5,470 | 12,100 | 1.8 | 2.6 | 1.7 | 3.8 |
| Hydrophobic TS-530 | 210 | 1,590 | 2,830 | 3,560 | 5,700 | 10,600 | 1.8 | 2.2 | 1.6 | 3.0 |

The permeation data show that the pure-gas permeabilities of PMP films filled with hydrophilic or hydrophobic silica types having surface areas of ≧200 m²/g were about 40–80% higher than those of the pure PMP film. The pure-gas selectivities of the filled PMP films are comparable to those of the pure PMP film.

Example 5
Effect of Filler Content on Pure-Gas Permeation Properties of Filled-PMP Films Filled PMP films were prepared as in Example 2 using a hydrophobic silica type, TS-530, with silica contents of 15, 25, 40, 45, and 50 wt %. The pure-gas permeability was measured at 50 psig feed pressure, 0 psig permeate pressure and a temperature of 25° C. The pure-gas permeabilities and the calculated selectivities of the filled and unfilled PMP films are shown in Table 3.

TABLE 3

| Silica Content (wt %) | Permeability (Barrer) | | | | | Selectivity | | | |
|---|---|---|---|---|---|---|---|---|---|
| | $N_2$ | $O_2$ | $CH_4$ | $H_2$ | $CO_2$ | $O_2/N_2$ | $CH_4/N_2$ | $H_2/CH_4$ | $CO_2/CH_4$ |
| 0 (pure PMP) | 820 | 1,670 | 1,870 | 3,920 | 7,320 | 2.0 | 2.3 | 2.1 | 3.9 |
| 15 | 860 | 1,800 | 1,940 | 4,040 | 7,570 | 2.1 | 2.3 | 2.1 | 3.9 |
| 25 | 1,190 | 2,310 | 2,710 | 4,890 | 9,170 | 1.9 | 2.3 | 1.8 | 3.4 |
| 40 | 1,850 | 3,280 | 4,340 | 6,430 | 11,500 | 1.8 | 2.3 | 1.5 | 2.7 |
| 45 | 2,270 | 3,930 | 5,260 | 7,920 | 13,000 | 1.7 | 2.3 | 1.5 | 2.5 |
| 50 | 2,650 | 4,720 | 6,390 | 9,150 | 14,500 | 1.8 | 2.4 | 1.4 | 2.3 |

The data in Table 3 show that the permeability of the filled PMP films increased for all gases as the filler content increased. The permeability increased about 2- to 3-fold for all gases for a PMP film filled with 50 wt % silica. The pure-gas selectivities for oxygen/nitrogen, hydrogen/methane, and carbon dioxide/methane decreased as the filler content increased. For these relatively non-condensable gas pairs, the selectivity is determined primarily by differences in the sizes and hence the diffusion coefficients of the gases. The loss of selectivity indicates that the addition of the filler to the PMP matrix created larger gaps in the interconnected free volume of the filled films, thereby increasing the diffusion coefficient of the larger molecule proportionately more than the smaller molecule. The selectivity of methane/nitrogen remained about the same as loading increased, because the methane and nitrogen molecules are similar in size, so both diffusion coefficients increased by roughly the same factor.

Examples 6–9
Mixed-Gas Permeation Properties of PMP and Filled-PMP Films

Examples 6–8
Effect of Filler Type on Mixed-Gas Permeation Properties of Filled-PMP Films Example 6

The mixed-gas permeation properties of the PMP and silica-filled PMP films prepared in Examples 1 and 2 were determined for a gas mixture containing 2 vol % n-butane/98 vol % methane. The filled PMP films contained 30 wt % silica (L-90, M-5, EH-5, and TS-530, respectively). The experiments were performed as in Example 4 for the pure-gas experiments, except at a feed pressure of 150 psig.

Figure 1:
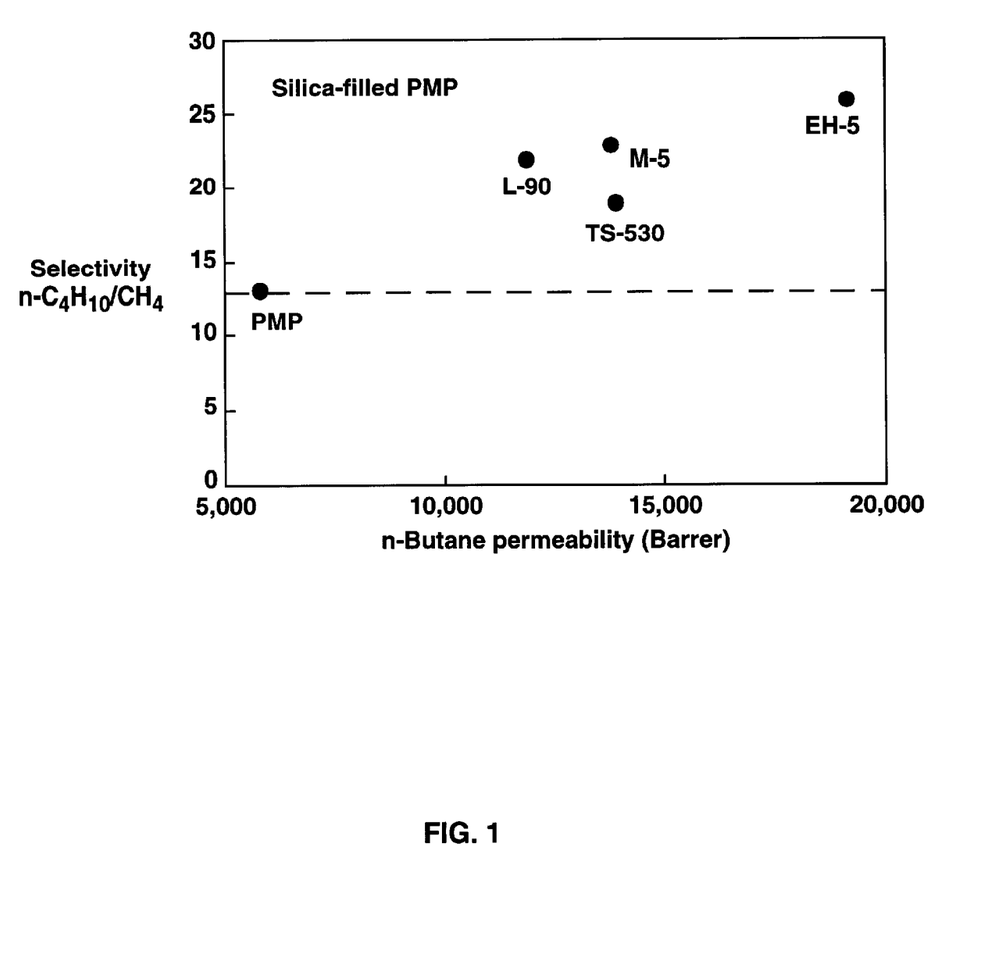
FIG. 1 is a plot of mixed-gas n-butane/methane selectivity against n-butane permeability for PMP films filled with 30 wt % of different grades of silica particles.

The mixed-gas permeation properties for silica-filled PMP films are compared to those of a pure PMP film for an n-butane/methane mixture in FIG. 1. The mixed-gas n-butane/methane selectivity of pure PMP was 13 and the n-butane permeability was about 6,000 Barrer. The addition of all fillers increased the n-butane permeability and the n-butane/methane selectivity permeability significantly.

The n-butane permeability and the n-butane/methane selectivity increased as the surface area of the filler particles increased, indicating that smaller particles lead to a more open polymer matrix. The best results were obtained with the EH-5 silica, which yielded an n-butane permeability of about 19,000 Barrer and a butane/methane selectivity of 26. This represents a three-fold increase in permeability and a two-fold increase in selectivity compared with the unfilled material. In fact, the n-butane/methane selectivity of silica-filled PMP is higher than that of any polymer known.

Example 7

The experiment of Example 6 was repeated with a gas mixture containing 20 vol % propylene/80 vol % nitrogen. The mixed-gas permeation properties of filled PMP films are compared to those of pure PMP in FIG. 2. The filled PMP films showed higher mixed-gas selectivities and higher permeabilities than those of a pure PMP film for propylene/nitrogen mixtures.

Figure 2:
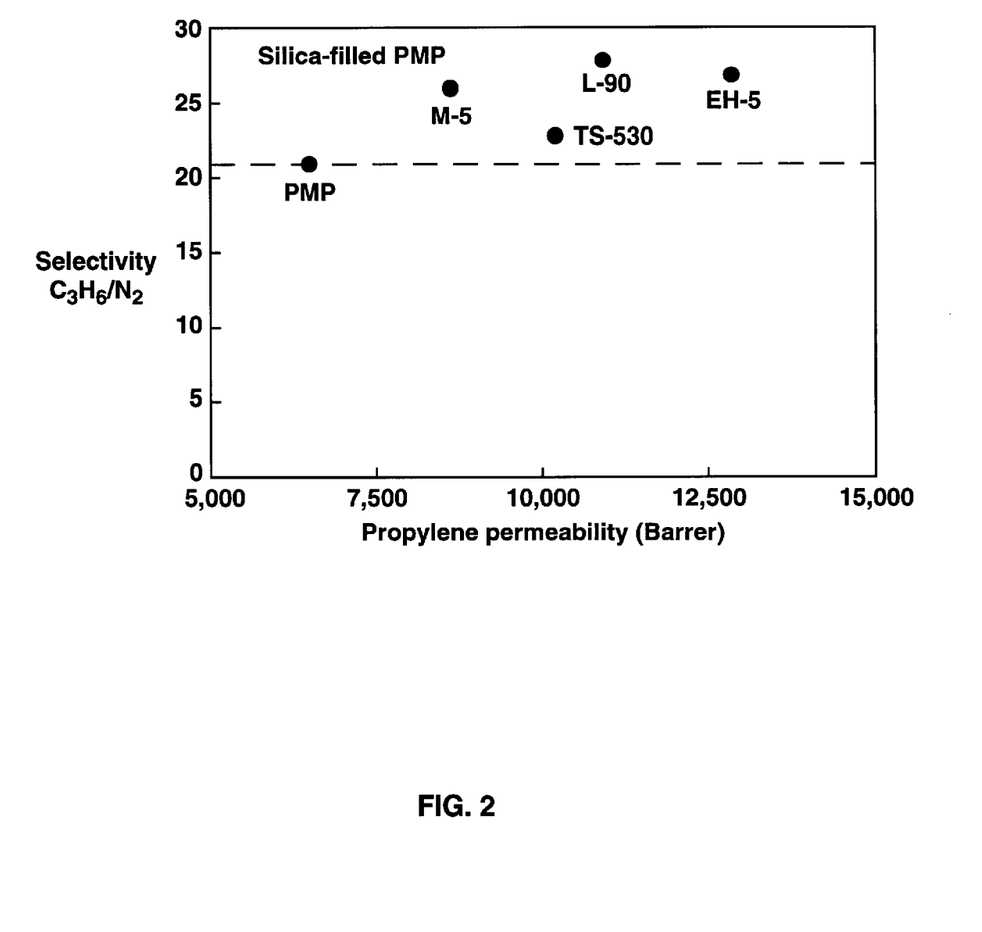
FIG. 2 is a plot of mixed-gas propylene/nitrogen selectivity against propylene permeability for PMP films filled with 30 wt % of different grades of silica particles.

The EH-5 silica filled PMP showed a propylene permeability more than double that of the unfilled PMP. The highest selectivity (28), representing an improvement of 40% over unfilled PMP, was obtained with the L-90 filler.

Example 8

The experiment of Example 6 was repeated with a gas mixture containing 10 vol % propane/90 vol % hydrogen.

Figure 3:
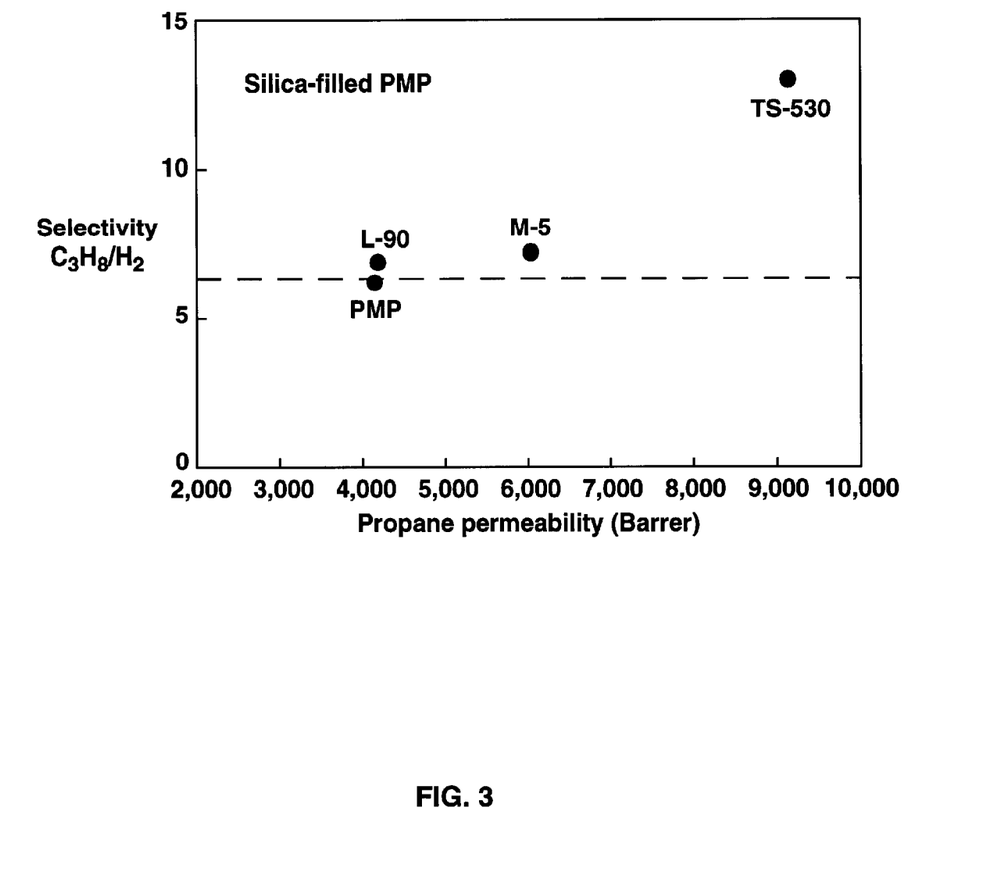
FIG. 3 is a plot of mixed-gas propane/hydrogen selectivity against propane permeability for PMP films filled with 30 wt % of different grades of silica particles.

The mixed-gas permeation properties of filled PMP films are compared to those of pure PMP in FIG. 3. The filled PMP films showed higher mixed-gas selectivities and higher permeabilities than those of a pure PMP film for propane/hydrogen mixtures.

The best results were obtained with the TS-530 filler, which more than doubled both the permeability and the selectivity compared with unfilled PMP.

Example 9
Effect of Filler Content on Permeation Properties of Filled PMP Films

Figure 4:
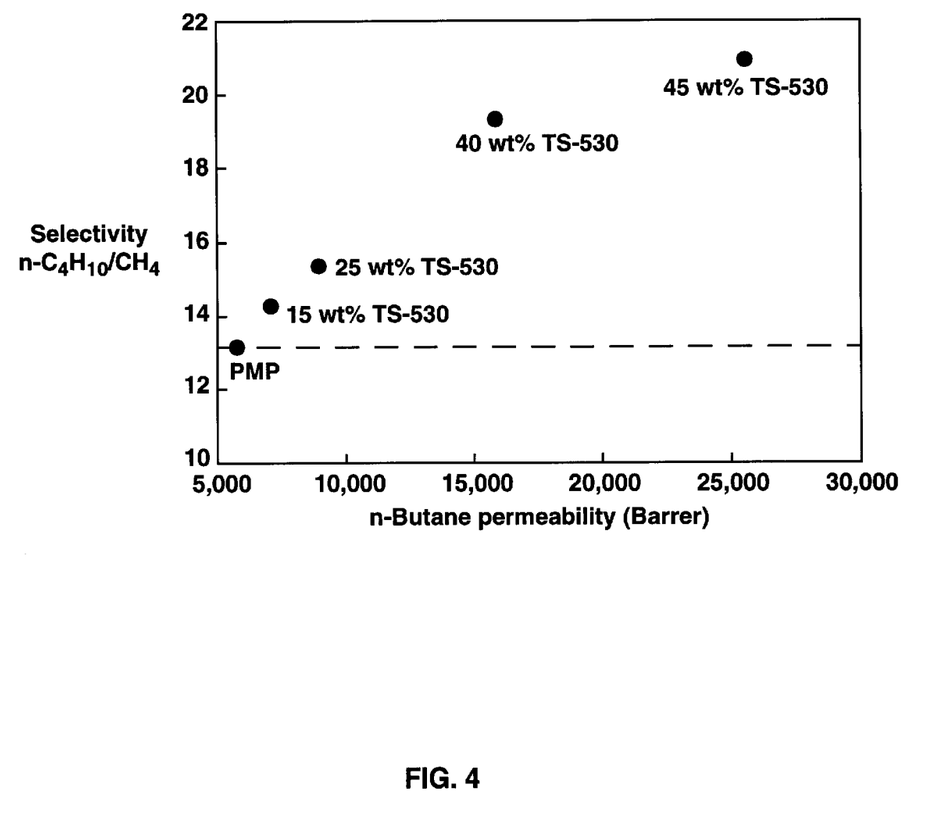
FIG. 4 is a plot of mixed-gas n-butane/methane selectivity against n-butane permeability for PMP films filled with different wt % loadings of TS-530 grade silica particles.

The effect of the silica content on the permeation properties of filled PMP films was determined with a 2 vol % n-butane/98 vol % methane gas mixture. The filler content of the PMP films was varied between 15 and 45 wt %, using a hydrophobic silica, TS-530. The feed pressure was 150 psig, the permeate pressure was atmospheric (0 psig), and the temperature was 25° C. The mixed gas permeabilities and selectivities of the filled and unfilled PMP films are shown in FIG. 4.

The n-butane permeability increased fourfold from about 6,000 Barrer for pure PMP film to about 25,000 Barrer for a PMP film containing 45 wt % silica. The mixed gas n-butane/methane selectivity increased from 13 for the pure PMP film to 21 for a PMP film containing 45 wt % silica.

These experimental results indicate that the gas separation properties increase as the filler loading increases.

Example 10
Mixed-Gas Permeation Properties of Filled PMP Thin-Film Composite Membranes Gas permeation measurements were carried out with a 2 vol % n-butane/98 vol % methane mixture as in Example 9, but using a composite membrane prepared as in Example 3, containing 30 wt % EH-5 silica filler in PMP. The thickness of the silica-filled PMP selective layer of the composite membrane was about 10 $\mu$m. The feed pressure was 100 psig, the permeate pressure was 0 psig, and the temperature was 25° C.

The membrane had a pressure-normalized n-butane flux of $1,200\times10^{-6}$ cm$^3$(STP)/cm$^2$·s·cmHg and an n-butane/methane selectivity of 17. This butane/methane selectivity is higher than that of an unfilled PMP film (13) but lower than that of a filled PMP film (100 $\mu$m thick) (26). The lower selectivity of the composite membrane can probably be attributed to transport resistance of the PVDF support or to concentration polarization due to the very high permeate flux.

SET 2: PTMSP Experiments and Results

Example 11
Polymer Film Preparation

The polymer, poly(1-trimethylsilyl-1-propyne) [PTMSP], was prepared in accordance with the procedure described in U.S. Pat. No. 4,755,193 to Higashimura et al. The polymer was dissolved in toluene (1–2 wt % solution), and the solution was cast onto glass plates. The resulting films were dried at ambient conditions for 24 hours, then dried under vacuum at 80° C. for three days to completely remove the solvent. The finished PTMSP films were 20–50 $\mu$m (±0.5 $\mu$m) thick, as determined with a precision micrometer.

Example 12
Filled-Polymer Film Preparation

Silica-filled PTMSP films were prepared by dispersing ultrafine silica particles (Cabot Corp., Tuscola, Ill.) in the PTMSP casting solution. The dispersion was mixed with a high-speed blender for 10 minutes and cast immediately onto glass plates. The silica-filled PTMSP films were dried as described in Example 11. The finished filled-PTMSP films were 50–200 $\mu$m (±0.5 $\mu$m) thick, as determined with a precision micrometer.

Table 4 lists the characteristics and the content (by weight) of two different silica types that were used for the filled PTMSP films.

TABLE 4

| Silica Type | Silica Content (wt %) | Surface Groups | Surface Area (m$^2$/g) | Approximate average particle diameter (Å) |
|---|---|---|---|---|
| EH-5 | 30 | hydroxyl (hydrophilic) | 380 | 80 |
| TS-610 | 50 | dimethylsilyl (hydrophobic) | 120 | 250 |

Example 13
Effect of Filler Type on Pure-Gas Permeation Properties of Filled-PTMSP Films Experiments were carried out to determine the pure-gas permeation properties of the PTMSP and filled-PTMSP films prepared in Examples 11 and 12. Samples of the films were cut into stamps and mounted in a permeation test-cell apparatus. The permeation of pure nitrogen, oxygen, methane, hydrogen, and carbon dioxide was measured at a feed pressure of 50 psig and a permeate pressure of 0 psig. The temperature was maintained at 25° C. The measurements were carried out with a constant pressure/variable volume method; the volumetric gas flow rates were determined with a bubble flow meter. The pure-gas permeabilities and the calculated selectivities of the filled and unfilled PTMSP films are shown in Table 5.

TABLE 5

| | Permeability (Barrer) | | | | | Selectivity | | | |
|---|---|---|---|---|---|---|---|---|---|
| Silica Type | N$_2$ | O$_2$ | CH$_4$ | H$_2$ | CO$_2$ | O$_2$/N$_2$ | CH$_4$/N$_2$ | H$_2$/CH$_4$ | CO$_2$/CH$_4$ |
| None (pure PTMSP) | 5,941 | 8,903 | 14,883 | 15,451 | 33,862 | 1.5 | 2.5 | 1.0 | 2.3 |
| Hydrophilic EH-5 | 7,849 | 10,795 | 19,971 | 18,786 | 37,923 | 1.4 | 2.5 | 0.94 | 1.9 |
| Hydrophobic TS-610 | 9,513 | 14,299 | 22,908 | 30,515 | 45,365 | 1.5 | 2.4 | 1.3 | 2.0 |

The permeation data show that the pure-gas permeabilities of the filled-PTMSP films range from about 10% to about 100% higher than those of the pure PTMSP film. The pure-gas selectivities of the filled-PTMSP films are comparable to those of the pure PTMSP film.

Example 14
Effect of Filler Type on Mixed-Gas Permeation Properties of Filled-PTMSP Films The mixed-gas permeation properties of the PTMSP and silica-filled PTMSP films prepared in Examples 11 and 12 were determined for a gas mixture containing 2 vol % n-butane/98 vol % methane. The filled PTMSP films contained 30 wt % EH-5 and 50 wt % TS-610 silica. The experiments were performed as in Example 13 for the pure-gas experiments, except at 150 psig feed pressure. The mixed-gas permeation properties for silica-filled PTMSP films are compared to those of a pure PTMSP film in Table 6.

TABLE 6

| Silica Type | Permeability (Barrer) | | Selectivity |
| --- | --- | --- | --- |
| | $C_4H_{10}$ | $CH_4$ | $C_4H_{10}/CH_4$ |
| None (pure PTMSP) | 39,249 | 1,891 | 21 |
| Hydrophilic EH-5 | 54,288 | 2,326 | 23 |
| Hydrophobic TS-610 | 114,655 | 4,980 | 23 |

The mixed-gas n-butane/methane selectivity of pure PTMSP was 21 and the n-butane permeability was about 39,000 Barrer. The addition of either filler to PTMSP increased the permeabilities significantly, and increased the mixed-gas selectivity by about 10%.

SET 3: Perfluoro-2,2-dimethyl-1,3-dioxole Experiments and Results

Example 15
Polymer Film Preparation

The polymer, perfluoro-2,2-dimethyl-1,3-dioxole [Teflon® AF 2400], was used as received from DuPont. The polymer was dissolved in FC-77 solvent (1–2 wt % solution), and the solution was cast onto glass plates. The resulting films were dried at ambient conditions for 24 hours, then dried under vacuum at 80° C. for three days to completely remove the solvent. The finished Teflon AF films were 20–50 μm (±0.5 μm) thick, as determined with a precision micrometer.

Example 16
Filled-Polymer Film Preparation

Silica-filled Teflon films were prepared by dispersing 18–40 wt % TS-530 silica particles in the Teflon casting solution. The dispersion was mixed with a high-speed blender for 10 minutes and cast immediately onto glass plates. The silica-filled Teflon films were dried as described in Example 15. The finished filled-Teflon AF films were 50–100 μm (±0.5 μm) thick, as determined with a precision micrometer.

Example 17
Effect of Filler Content on Pure-Gas Permeation Properties of Filled-Teflon AF Films Pure and filled-Teflon AF films were prepared as in Examples 15 and 16, and the pure-gas permeabilities were measured at 50 psig feed pressure, 0 psig (atmospheric) permeate pressure and a temperature of 25° C. The pure-gas permeabilities and the calculated selectivities of the filled and unfilled Teflon AF films are shown in Table 7.

TABLE 7

| Silica Content | Permeability (Barrer) | | | | | | Selectivity | | | | |
| --- | --- | --- | --- | --- | --- | --- | --- | --- | --- | --- | --- |
| (wt %) | $N_2$ | $O_2$ | $CH_4$ | $H_2$ | $CO_2$ | $C_4H_{10}$ | $O_2/N_2$ | $CH_4/N_2$ | $H_2/CH_4$ | $CO_2/CH_4$ | $C_4H_{10}/CH_4$ |
| 0 (pure Teflon AF) | 570 | 1,170 | 410 | 2,420 | 2,950 | 670 | 2.1 | 0.71 | 5.9 | 7.2 | 1.6 |
| 18 | 970 | 1,920 | 880 | 3,930 | 4,850 | 1,300 | 2.0 | 0.90 | 4.5 | 5.5 | 1.5 |
| 30 | 1,980 | 3,516 | 2,000 | 6,850 | 8,540 | 3,540 | 1.8 | 1.0 | 3.4 | 4.3 | 1.8 |
| 40 | 3,500 | 5,850 | 4,200 | 11,500 | 13,990 | 27,680 | 1.7 | 1.2 | 2.7 | 3.3 | 6.6 |

The data in Table 7 show that the permeability of the filled Teflon AF films increased significantly for all gases as the filler content increased. As with the filled PTMSP films, the pure-gas selectivities for oxygen/nitrogen, hydrogen/methane, and carbon dioxide/methane decreased as the filler content increased. The calculated methane/nitrogen selectivity indicates that the unfilled and low-loaded Teflon AF films were actually nitrogen, rather than methane, selective. Only when the filler content reached 40 wt % did the film become methane-selective for the gas pair. The calculated n-butane/methane selectivities showed little change for the pure and low-loaded Teflon AF films. When the filler content reached 40 wt %, the butane/methane selectivity increased significantly.

Example 18
Effect of Filler Content on Mixed-Gas Permeation Properties of Filled-Teflon AF Films The mixed-gas permeation properties of the unfilled and silica-filled Teflon AF films prepared in Examples 15 and 16 were determined for a gas mixture containing 2 vol % n-butane/98 vol % methane. The experiments were performed as in Example 17, except at a feed pressure of 150 psig. The mixed-gas permeation properties for silica-filled Teflon AF films are compared to those of a pure Teflon AF film in Table 8.

TABLE 8

| Silica Content | Permeability (Barrer) | | Selectivity |
| --- | --- | --- | --- |
| (wt %) | $C_4H_{10}$ | $CH_4$ | $C_4H_{10}/CH_4$ |
| 0 (pure Teflon AF) | 300 | 530 | 0.57 |
| 18 | 840 | 870 | 0.97 |
| 30 | 1,980 | 1,480 | 1.3 |
| 40 | 9,292 | 3,744 | 2.5 |

The results show that the addition of the filler to Teflon AF had a dramatic effect on permeability of both gases. The unfilled and low-loaded Teflon AF films were butane-rejecting in these mixed gas experiments. When the filler content reached 30–40 wt % the films became butane-selective.

We claim:

1. A process for separating a component of a first fluid mixture, comprising the following steps:
   (a) providing a membrane having a feed side and a permeate side, the membrane comprising a separating layer of a polymer having a glass transition temperature, $T_g$, of at least about 100° C. and a fractional free volume of at least about 0.20, throughout which separating layer are dispersed fine non-porous particles having an average particle diameter no greater than about 1,000 Å;
   (b) passing the first fluid mixture across the feed side;
   (c) providing a driving force for transmembrane permeation;
   (d) withdrawing from the permeate side a second fluid mixture enriched in the component compared with the first fluid mixture.

2. The process of claim 1, wherein the first fluid mixture is a gas.

3. The process of claim 1, wherein the first fluid mixture is a liquid.

4. The process of claim 1, wherein the first fluid mixture is a liquid and the second fluid mixture is a gas.

5. The process of claim 1, wherein the component comprises a condensable component.

6. The process of claim 1, wherein the component comprises an organic compound.

7. The process of claim 1, wherein the component comprises a $C_{3+}$ hydrocarbon.

8. The process of claim 1, wherein the first fluid mixture comprises $C_{3+}$ hydrocarbons and hydrogen.

9. The process of claim 1, wherein the first fluid mixture comprises a refinery gas stream.

10. The process of claim 1, wherein the first fluid mixture comprises natural gas.

11. The process of claim 1, wherein the first fluid mixture is a liquid containing mixed organic components.

12. The process of claim 1, wherein the first fluid mixture comprises an alcohol and water.

13. The process of claim 1, wherein the polymer comprises poly(4-methyl-2-pentyne).

14. A gas separation process comprising the steps of:
   (a) providing a membrane having a feed side and a permeate side, the membrane comprising a separating layer of a polymer having a glass transition temperature, $T_g$, of at least about 100° C. and a fractional free volume of at least about 0.20, throughout which separating layer are dispersed fine non-porous particles having an average particle diameter no greater than about 1,000 Å;
   (b) passing a first gas mixture containing a component to be separated across the feed side;
   (c) providing a driving force for transmembrane permeation;
   (d) withdrawing from the permeate side a second gas mixture enriched in the component compared with the first gas mixture.

15. The process of claim 14, wherein the polymer comprises poly(4-methyl-2-pentyne).

16. The process of claim 14, wherein the first gas mixture comprises a $C_{3+}$ hydrocarbon and hydrogen.

17. The process of claim 14, wherein the first gas mixture comprises a $C_{3+}$ hydrocarbon and methane.

18. A process for recovering hydrogen from a gas mixture of hydrocarbons and hydrogen, comprising the steps of:
   (a) providing a membrane having a feed side and a permeate side, the membrane comprising a separating layer of a polymer having a glass transition temperature, $T_g$, of at least about 100° C. and a fractional free volume of at least about 0.20, throughout which separating layer are dispersed fine non-porous particles having an average particle diameter no greater than about 1,000 Å;
   (b) passing the gas mixture across the feed side;
   (c) providing a driving force for transmembrane permeation;
   (d) withdrawing from the permeate side a permeate gas mixture enriched in hydrocarbons compared with the gas mixture;
   (e) withdrawing from the feed side a residue gas mixture enriched in hydrogen compared with the gas mixture.

19. A process for separating a first hydrocarbon component from a second hydrocarbon component in a mixture thereof, comprising the following steps:
   (a) providing a membrane having a feed side and a permeate side, the membrane comprising a polymeric support layer on which is coated a separating layer of a polymer having a glass transition temperature, $T_g$, of at least about 100° C., throughout which separating layer are dispersed fine non-porous particles having an average particle diameter no greater than about 1,000 Å;
   (b) passing the mixture across the feed side;
   (c) providing a driving force for transmembrane permeation;
   (d) withdrawing from the permeate side a permeate mixture enriched in the first hydrocarbon component compared with the mixture.

20. The process of claim 19, wherein the first hydrocarbon component is an unsaturated hydrocarbon and the second hydrocarbon component is a saturated hydrocarbon.

21. The process of claim 19, wherein the first hydrocarbon component is a linear hydrocarbon and the second hydrocarbon component is a branched hydrocarbon.

22. A membrane comprising a separating layer of a polymer having a glass transition temperature, $T_g$, of at least about 100° C. and a fractional free volume of at least about 0.20, within which polymer are dispersed fine non-porous particles having an average particle diameter no greater than about 1,000 Å.

23. The membrane of claim 22, further comprising a support layer on which the separating layer is coated.

24. The membrane of claim 22, wherein the polymer is characterized by a nitrogen permeability at room temperature of at least about 50 Barrer.

25. The membrane of claim 22, wherein the polymer comprises a substituted polyacetylene.

26. The membrane of claim 22, wherein the polymer comprises a disubstituted polyacetylene.

27. The membrane of claim 22, wherein the polymer comprises poly(1-trimethylsilyl-1-propyne).

28. The membrane of claim 22, wherein the polymer comprises poly(4-methyl-2-pentyne).

29. The membrane of claim 22, wherein the particles have an average specific surface area of at least about 100 m$^2$/g.

30. The membrane of claim 22, wherein the particles have an average specific surface area of at least about 200 m$^2$/g.

31. The membrane of claim 22, wherein the particles comprise silica.

32. The membrane of claim 22, wherein the particles comprise carbon black.

33. The membrane of claim 22, wherein the particles are dispersed at a loading of at least about 20 wt % in the polymer.

34. The membrane of claim 22, wherein the particles are dispersed at a loading of at least about 30 wt % in the polymer.

35. The membrane of claim 22, wherein the particles are dispersed at a loading of at least about 40 wt % in the polymer.

36. The membrane of claim 22, wherein the membrane has a mixed-gas n-butane/methane selectivity of at least about 10.

37. The membrane of claim 22, wherein the membrane has a mixed-gas propane/nitrogen selectivity of at least about 10.

38. The membrane of claim 22, wherein the membrane has a mixed-gas propane/hydrogen selectivity of at least about 10.

* * * * *